United States Patent [19]

Pollock

[11] Patent Number: 5,354,671
[45] Date of Patent: Oct. 11, 1994

[54] ENZYMATIC CLARIFICATION OF POLYSACCHARIDES

[75] Inventor: Thomas J. Pollock, San Diego, Calif.

[73] Assignees: Shin-Etsu Chemical Co., Ltd., Tokyo, Japan; Shin-Etsu Bio, Inc., San Diego, Calif.

[21] Appl. No.: 906,262

[22] Filed: Jun. 26, 1992

[51] Int. Cl.$^5$ .................. C12P 19/04; C12P 19/06; C12N 9/00
[52] U.S. Cl. .................. 435/101; 435/104; 435/183; 435/822; 435/828
[58] Field of Search .............. 435/183, 220, 828, 100, 435/101, 104, 822, 832, 874, 911

[56] References Cited

U.S. PATENT DOCUMENTS

| | | | |
|---|---|---|---|
| 3,355,447 | 11/1967 | O'Connell | 260/209 |
| 3,516,983 | 6/1970 | Colegrove | 260/209 |
| 3,658,650 | 4/1972 | Okazaki | 435/822 |
| 3,964,972 | 6/1976 | Patton | 195/31 P |
| 3,966,618 | 6/1976 | Colegrove | 435/104 |
| 3,996,618 | 12/1976 | Suzuki | 360/96 |
| 4,010,071 | 3/1977 | Colegrove | 435/832 |
| 4,094,739 | 6/1978 | Schroeck | 195/7 |
| 4,119,491 | 10/1978 | Wellington | 195/7 |
| 4,135,979 | 1/1979 | Corley et al. | 195/31 P |
| 4,165,257 | 8/1979 | Stokke | 435/262 |
| 4,416,990 | 11/1983 | Rinavdo et al. | 435/911 |
| 4,431,734 | 2/1984 | Rinavdo et al. | 435/104 |
| 4,481,294 | 11/1984 | Downs | 435/874 |

FOREIGN PATENT DOCUMENTS

| | | |
|---|---|---|
| 0039962 | 11/1981 | European Pat. Off. . |
| 0049012 | 4/1982 | European Pat. Off. . |
| 0078621 | 5/1983 | European Pat. Off. . |
| 18600779 | 10/1987 | Netherlands . |
| 2065689 | 7/1981 | United Kingdom . |

OTHER PUBLICATIONS

Pollock, et al., "J. of Indusstrial Microbiology", vol. 11 (3), 1993, pp. 187–192.

Primary Examiner—Douglas W. Robinson
Assistant Examiner—Kristin Larson
Attorney, Agent, or Firm—McAulay Fisher Nissen Goldberg & Kiel

[57] ABSTRACT

A novel enzyme composition capable of lysing or digesting cells or cellular debris of polysaccharide-producing bacteria in the presence of the exopolysaccharides without any significant degradation of the exopolysaccharides. Methods for preparing the enzyme composition, using the composition to clarify mixtures of polysaccharides and cellular debris, and pure cultures for making the enzyme are disclosed.

12 Claims, No Drawings

ENZYMATIC CLARIFICATION OF POLYSACCHARIDES

BACKGROUND OF THE INVENTION

This invention pertains to the field of purification and/or clarification of exopolysaccharides, i.e., polysaccharides produced by microorganisms (referred to herein as polysaccharide-producing bacteria). In particular, this invention relates to methods for the removal of cellular debris and the like which normally accompany fermentation processes utilizing the microorganisms which produce polysaccharides.

Such exopolysaccharides can be precipitated directly from fermentation broths by the addition of an organic solvent in which they are insoluble, e.g., isopropyl alcohol (IPA) and then dried. A solution of the crude or technical-grade polysaccharide in water is turbid due to the presence of cellular debris and insoluble components from the fermentation medium. As used herein, cellular debris includes dead cells and portions thereof present in fermentation broths and precipitated material therefrom in exopolysaccharide production fermentations.

For many end use applications, the particulate contaminating material is undesirable and a more pure product is required. However, procedures to clarify or purify the desired products add complexity and additional cost to the production process.

A typical example of such a polysaccharide is xanthan gum (sometimes referred to herein as xanthan). Thus, for example, when xanthan is used for tertiary oil recovery, the particulate material present in the crude xanthan plugs the pores of the oil-bearing rock formation, thereby reducing oil flow. Also, in cosmetic end uses, wherein xanthan is used as a viscosity control agent, the formulations often require transparency and the xanthan gum must have a high purity.

In order to clarify fermentation broths containing xanthan, chemical, mechanical and enzymatic treatments have been used. Mechanical clarification by either centrifugation or filtration is difficult and time consuming due to the extreme viscosity of the fermentation broths, even though the process can be somewhat improved by warming the xanthan before filtration. See U.S. Pat. No. 4,135,979.

Chemical clarification is carried out by the addition to the fermentation broth of alkali as disclosed in U.S. Pat. Nos. 3,355,447 and 3,964,972 or hypochlorite, as disclosed in U.S. Pat. Nos. 3,516,983, and 3,996,618. However, these chemical treatments also result in deacetylation and degradation of the xanthan polymers.

Several enzymatic methods for clarification of xanthan have been described. See U.S. Pat. Nos. 4,010,071; 4,165,257; GB Patent Application 2,065,689; European Patent Appl. 0,039,962; European Patent Appl. 0,078,621; and U.S. Pat. No. 4,119,491. Each method includes the use of an acidic, neutral or alkaline protease of the type obtained from gram-positive bacteria or fungi. The optimal reaction time, temperature and pH are specific for each enzyme. In at least one case, the enzymatic preparation includes both protease and glucanase activities. See European Patent Application No. 0,039,962.

A variation of the enzymatic method is to add viable and large-sized *Trichoderma viride* fungal cells to the xanthan broth to consume the xanthan-producing cells. See U.S. Pat. No. 4,094,739. However, this also requires filtration to remove the fungal cells from the viscous fermentation broth.

Generally, it has been thought that gram-negative bacteria would be less likely to serve as a useful source of enzymes for the lysis of other gram-negative microorganisms. This is based on the assumption that the enzyme-secreting bacteria might themselves be damaged by the lytic enzymes that they secrete. As a result, efforts at clarification of cultures of the gram-negative *Xanthomonas campestris* have thus far focused on the proteolytic enzymes of the gram-positive bacteria, such as, *Bacillus subtilis*, and eukaryotic fungi.

SUMMARY OF THE INVENTION

I have discovered a novel enzyme composition capable of lysing or digesting cells or cellular debris of polysaccharide-producing bacteria in the presence of the exopolysaccharides without any significant degradation of the exopolysaccharides. I have further discovered a method for preparing the inventive enzyme by the culturing of microorganisms of the genus types Aeromonas, Micropolyspora, and Lysobacter. In addition, I have discovered biologically pure cultures of Aeromonas and Lysobacter species which are capable of producing the inventive enzyme composition and a method for selecting the inventive strain. The inventive enzyme compositions may be used to clarify mixtures of polysaccharides and the cellular debris produced by the submerged culturing of the above listed organisms without any significant detrimental effect on the polysaccharides in the mixture.

DETAILED DESCRIPTION OF THE INVENTION

More particularly, the inventive enzyme composition is one which is capable of clarifying mixtures of polysaccharides and cellular debris produced by a submerged culturing of bacteria. The inventive enzyme is particularly useful for clarifying mixtures of polysaccharides from *Xanthomonas campestris*, Pseudomonas, Alcaligenes, and *Beijerinckia indica*. The "inventive enzyme" is sometimes referred to herein as the "enzyme composition". These terms are used interchangeably herein. Thus, the inventive enzyme may be a single enzyme or mixture of enzymes produced by the respective organism. In addition, the inventive enzyme may differ from organism to organism. However, the inventive enzyme from each of the organisms share the crucial characteristic, namely, the ability to clarify mixtures of polysaccharides and the cellular debris produced by a given organism by lysing the cellular debris from the produced organism and not have any significant adverse effect on the polysaccharide itself.

As used herein, the term "clarifying" or "clarification" in connection with mixtures of polysaccharides with cellular debris, means that the cellular debris is lysed or otherwise degraded so that it can be easily separated from the polysaccharide, as by washing and the like and the polysaccharide can be recovered in a purified form.

The enzyme composition is obtained by subjecting a collection of wild-type strains to culturing in a nutrient medium. Optionally, the medium may contain dead cells and/or the cellular and bacterial debris of the bacteria to be clarified, as a carbon source. As used herein, the expression "wild-type" with respect to such strains means a collection of natural strains which are obtained directly from nature, e.g., from a soil sample, floor, and the like.

From these culturing steps, strains which survive are selected and are further subjected to submerged fermentation in a growth medium which again contains as a predominant carbon source dead cells and/or cellular debris of the bacteria. Upon completion of and/or during this fermentation, a culture broth containing the inventive enzyme composition is physically separated from the producing microorganisms. The enzyme composition is contained within the culture medium. The fermentation conditions utilized are those which are known and conventional in the art.

I have also found that the inventive enzyme composition can be desirably produced by subjecting a strain which is from the group of Aeromonas, Lysobacter or Mycropolyspora to fermentation conditions in growth media, and then separating the broth which contains the enzyme composition from the producing microorganism.

In addition, we have discovered that a novel biologically pure culture of a strain of Aeromonas and Lysobacter species is capable of producing an enzyme in accordance with the invention.

With the inventive enzyme, it is possible to clarify a mixture of a polysaccharide which is produced by the submerged culturing of a bacteria and the cellular debris of the bacteria by treating the mixture with the inventive enzymic composition. The conditions for this treatment will depend on the particular polysaccharide and bacteria from which it is obtained. Generally, however, it is necessary only to mix the enzyme composition with the mixture of the polysaccharide and cellular debris and treat the mixture at a temperature in the range from about 20° C. to 80° C. for a time period of from about 1 to 10 hours so as to allow the enzyme to completely digest the cellular debris.

The following examples describe the inventive method for isolating bacteria from the genus Aeromonas. See Bergey's Manual of Systematic Bacteriology, pp. 545–548,; eds. N. R. Krieg & J. G. Holt, Williams and Wilkins, Baltimore, Md. (1984). These organisms were isolated from soil samples and produce lytic enzymes that lyse *X. campestris*. In addition, several isolates of *Lysobacter enzymogenes* (ATCC 27796, 29489, 29482, 29483, 29484 and 29488), a gram-negative bacteria (See P. Christensen & F. D. Cook, Int. J. Systematic Bacteriology 28: 367–393 (1978), and an isolate of *Micropolyspora faeni* (ATCC 21450), an actinomycete, See U.S. Pat. No. 3,713,983, were tested for lysis of Xanthomanas cells and shown to cause clarification of cell cultures.

EXAMPLE 1

Isolation of Microorganisms that Clarify Xanthomonas Cellular Debris Suspended in Nutrient Agar Damp soil was collected from a site within one yard from the outflow of household laundry grey water at a residence on Palomar Mountain, San Diego County, California. About one-half volume of municipal tap water was added to the uncompacted soil to create a slurry and left at about 25° C. for one day. A mutant of *Xanthomonas campestris* B1459 (strain X74) that does not synthesize xanthan gum (strain X74) was grown in Luria broth at 30° C. to stationary phase. Strain X74 is the same as "X59m9" referred to in Table 1 of the Thorne, et al, *J. Bact.* 169: 3593–3600 (1987 ).

The cells were concentrated by centrifugation, autoclaved to kill the cells and about one-third of the concentrated killed cells was added to the soil suspension every other day. After about a week at 25° C. with intermittent stirring (3 times per day), a sample of 10 ml was removed from the slurry, allowed to settle and then the clarified liquid was transferred to a fresh tube. After diluting 100-fold into P2 salts, about 1 μl was spread onto agar plates containing P2 salts and Xanthomonas strain X74 cells that had first been autoclaved to kill the cells. Enough cellular material is included in the plate to cause the agar to appear cloudy or nontransparent (partially opaque).

| COMPOSITION OF P2 SALTS |
|---|
| 1 g $(NH_4)_2HPO_4$ |
| 2 g $K_2HPO_4$ |
| 0.5 g NaCl |
| 0.05 g $MgSO_4$—$7H_2O$ |
| DI to 1 liter |
| pH was adjusted to 7.6 |

After incubation for three days at 28° C., about 200–400 colonies formed from the wild-type strains in the soil on each plate and about one-half of the colonies were surrounded by zones of clearing of the opaque Xanthomonas cells and debris. Nine colonies surrounded by the largest clear zones were purified by replating onto agar plates containing Luria broth. Each colony was then retested for clearing of Xanthomonas cells and cell debris on agar plates prepared as above. Aeromonas isolates 1, 2, 4, 5 and 7 were retained as representative of the types of colony appearances observed. Other isolates were observed as likely duplicates of these five isolates, based on gross colony appearance, and were not retained.

EXAMPLE 2

Taxonomic Classification of the Xanthomonas-hydrolyzing Soil Isolates

Standard tests were performed to identify the newly isolated bacteria from Example 1. See Color Atlas and Textbook of Diagnostic Microbiology, ( eds. E. W. Koneman et al ) J. B. Lippincott Company, Philadelphia ( 1988 ). The results of the tests and observations are given below. The results indicate that each isolate is a gram-negative facultative anaerobe in the family: Vibrionaceae. See Bergey's Manual of Systematic Bacteriology.

Colony appearance: round, raised, shiny, buff or light-beige, iridescent surface, and translucent (isolates 1, 2, 5 & 7) or opaque (isolate 4) on nutrient agar plates.

Microscopic appearance: motile short rods. Length:-width ratio was about 1.7:1 and length was about ½ of *E. coli* K12 strain HB101.

Gram stain: Ambiguous Gram stain; however each strain was resistant to 20 μg/ml vancomycin and sensitive to 10 μg/ml of polymyxin. Loopfuls of bacteria became viscous upon immersion in 3% (w/v) KOH. The drug resistances and lysis in KOH are typical of gram-negative bacteria.

Cytochrome oxidase: positive (Kovac's spot test).

Catalase: positive (gas from 3% $H_2O_2$).

Indole production: positive.

Phenylalanine deaminase: negative.

Methyl red/Voges-Proskauer:

[MR] red (acid from glucose);
[VP] yellow (no acetoin produced).
Kligler iron agar:
  red (alkaline) slant, yellow (acid) butt;
  no gas ($CO_2$ or $H_2$);
  no $H_2S$ produced from thiosulfate;
  $H_2S$ produced from cysteine.

A series of tests were carried out to determine the genus of the inventive strain. All isolates (1, 2, 5 and 7) were identified by the following tests.:

| Resistance to | |
|---|---|
| 2,4 diamino-6,7-diisopropylpteridine (DDPP): | positive. |
| Growth on TCBS* plates: | negative. |
| Growth on LB + 6% NaCl: | negative. |
| Requirement for 0.6% NaCl: | negative. |
| Gelatin liquefaction: | positive. |
| Casein hydrolysis: | positive. |
| Starch hydrolysis: | positive. |
| Xanthomonas lysis and clearing: | positive. |
| Pigmentation: | negative. |
| Acid from sucrose and galactose: | positive. |
| Resistance to ampicillin (30 μg/ml) | positive. |

*Thiosulfate-citrate-bile-sucrose medium (Difco Co.)

These results show that the Genus is Aeromonas, and is not Vibrio, Plesiomonas, Photobacterium or Chromobacterium. By contrast, Vibrios are sensitive to DDPP, grow on TCBS agar plates and grow with 6% NaCl. Plesiomonads are sensitive to DDPP and KCN, do not secrete enzymes and do not produce acid from sucrose. Chromobacteria are purple pigmented, do not ferment sucrose or galactose, and do not hydrolyze starch. Photobacteria require 0.6% NaCl for growth, do not hydrolyze starch and do not ferment sucrose.

Within the genus Aeromonas, the presence of motile rods, absence of coccobacilli in chains and clumps, and growth in nutrient broth at 35°–37° C. eliminates *A. salmonicida* and subspecies from consideration. The remaining Aeromonas species found in the Bergey's Manual (1984) are: *A. hydrophila, A. caviae,* and *A. sobria.*

Table 1 sets forth a comparison of the traits for each of these species and the traits observed for the new isolates 1, 2, 4, 5 and 7 of Aeromonas. The numbers for the species are from a compilation of the frequencies reported in the following three studies: Janda, J. M., Reitano, M. and Bottone, E. J. (1984) J. Clin. Microbiol. 19: 44–47; Figura, N., Marri, L., Verdiani, S., Ceccherini, C. and Barberi, A. (1986) J. Clin. Microbiol. 23: 595–599; and Sakazaki, R. and Balows, A. (1981) In: The Prokaryotes Starr, M., Stolp, H., Truper, H. G., Balows, A. and Schlegel, H. G., eds. ) Springer-Verlag, Berlin. These numbers represent the number of isolates exhibiting the trait divided by the total number of isolates observed. Where numbers are not available, we show the "typical" result found in Bergey's Manual. "Typical" in Bergey's Manual means that more than 80% of isolates show a given trait.

These results show that the new deromona isolates 1, 2, 4, 5 and 7 are most closely related to *Aeromonas hydrophila* and *Aeromonas caviae,* although significant differences exist.

TABLE 1

| Discriminating Traits | A.h.[1] | A.c.[2] | A.s.[3] | 1 | 2 | 4 | 5 | 7 |
|---|---|---|---|---|---|---|---|---|
| Esculin hydrolysis | + 272/274 | + 146/148 | − 81/85 | + | + | + | + | + |
| KCN growth | + 266/274 | + 145/148 | − 76/85 | + | + | + | + | + |
| L-histidine as C-source | + "typically" | + Bergey's | − | + | + | + | + | + |
| L-arginine as C-source | + "typically" | + Bergey's | − | + | + | + | + | + |
| L-arabinose as C-source | + "typically" | + Bergey's | − | + | + | + | + | + |
| Gas from glucose | + 268/272 | − 148/148 | + 82/85 | − | − | − | − | − |
| Elastin hydrolysis | + 70/74 | − 62/62 | + 39/45 | − | − | − | − | − |
| $H_2S$ from cysteine | + 71/72 | − 60/62 | + 45/45 | + | + | + | + | + |
| Gluconate oxidation | + 6/6 | − 26/26 | + 5/5 | + | + | + | + | + |
| Arbutin hydrolysis | + 253/264 | + 145/145 | − 73/75 | − | − | + | − | − |

[1] A.h., *Aeromonas hydrophila*
[2] A.c., *Aeromonas caviae*
[3] A.s., *Aeromonas sobria*

Table 2 is arranged similarly, but shows less discriminating or nondiscriminating traits:

TABLE 2

| Traits | A.h. | A.c. | A.s. | 1 | 2 | 4 | 5 | 7 |
|---|---|---|---|---|---|---|---|---|
| Acetoin production | + 242/272 | − 146/148 | + 57/85 | − | − | − | − | − |
| Acid from salicin | + 229/274 | + 136/148 | − 84/85 | − | − | − | − | − |
| Acid from cellobiose | − 173/264 | + 122/145 | + 41/75 | + | + | + | + | + |
| Acid from arabinose | + 196/274 | + 136/148 | − 74/85 | − | − | − | − | − |
| Acid from mannose | + 63/64 | − 42/59 | − 22/35 | + | + | + | + | + |
| Acid from lactose | + 173/264 | + 83/140 | − 58/75 | − | − | − | − | − |
| Hemolysis (sheep RBC) | + 59/64 | − 53/59 | + 31/35 | − | − | − | − | − |
| Lysine decarboxylase | − 201/264 | − 144/145 | − 40/75 | − | − | − | − | − |
| Arginine dihydrolase | + 174/200 | + 86/86 | + 28/40 | − | − | + | − | − |
| Ornithine decarboxylase | − 200/200 | − 86/86 | − 40/40 | − | − | − | − | − |

Table 3 sets forth the pattern of utilization of carbohydrates for the Aeromonas isolates in two different media, OF basal and MacConkeys (Difco). The "OF basal" medium included per liter: 10 g peptone, 5 g NaCl and 18 mg phenol red. A "+" indicates utilization of the carbohydrate source.

TABLE 3

| | Medium | | | | | | | | |
|---|---|---|---|---|---|---|---|---|---|
| | OF Basal Isolate | | | | | MacConkey's Agar Isolate | | | |
| Carbohydrate Source | 1 | 2 | 4 | 5 | 7 | 1 | 2 | 4 | 5 | 7 |
| glucose | + | + | + | + | + | + | + | + | + | + |
| maltose | + | + | + | + | + | + | + | + | + | + |
| galactose | + | + | + | + | + | + | + | + | + | + |
| fructose | + | + | + | + | + | + | + | + | + | + |
| sucrose | + | + | + | + | + | + | + | + | + | + |
| rahmnose | − | + | − | − | − | − | + | − | − | − |
| raffinose | − | − | − | − | − | − | − | − | − | − |

The Aeromonas isolates were further identified using the Microlog ™ 1 software and GN-Microplates ™ obtained from Biolog, Inc. of Hayward, Calif. The basis for the identification is the metabolic oxidation of compounds arrayed in a 96 well microtiter plate. See B. R. Bochner, Nature 339: 157–158 (1989).

The database for comparison included 569 species or subgroups of gram-negative bacteria including 18 species and subspecies of Aeromonas. Each of the isolates most closely matched the profile for Aeromonas media-like DNA group 5A. The 18 species for comparison included:

1) *Aeromonas caviae* DNA group 4
2) Aeromonas DNA group 11
3) *Aeromonas eucrenophila* DNA group 6
4) *Aeromonas hydrophila* DNA group 1
5) *Aeromonas hydrophila*-like DNA group 2
6) *Aeromonas hydrophila*-like DNA group 3
7) *Aeromonas jandaei* DNA group 9
8) *Aeromonas media* DNA group 5B
9) *Aeromonas media*-like DNA group 5A
10) *Aeromonas salmonicida*
11) *Aeromonas salmonicida* subsp. achromogenes
12) *Aeromonas salmonicida* subsp. masoucida
13) *Aeromonas salmonicida* subsp. salmonicida
14) *Aeromonas schubertii* DNA group 12
15) *Aeromonas sobria* DNA group 7
16) *Aeromonas trota*
17) *Aeromonas veronii* DNA group 10
18) *Aeromonas veronii*-like DNA group 8

The results of the Microlog identification test are set forth in Table 4. In Table 4, "+" indicates oxidation of compound, "−" indicates no oxidation, and " " indicates a borderline reaction.

TABLE 4

| | | Isolate | | | | |
|---|---|---|---|---|---|---|
| | | 1 | 2 | 4 | 5 | 7 |
| A1 | water | − | − | − | − | − |
| A2 | α-cyclodextrin | − | − | − | | − |
| A3 | dextrin | + | + | + | + | + |
| A4 | glycogen | + | + | + | + | + |
| A5 | tween 40 | + | | + | + | + |
| A6 | tween 80 | + | + | + | + | + |
| A7 | N-acetyl-D-galactosamine | − | − | − | − | − |
| A8 | N-acetyl-D-glucosamine | + | + | + | + | + |
| A9 | adonitol | − | − | − | − | − |
| A10 | L-arabinose | + | + | + | + | + |
| A11 | D-arabitol | − | − | − | − | − |
| A12 | cellobiose | + | + | + | + | + |
| B1 | i-erythritol | − | − | − | − | − |
| B2 | D-fructose | + | + | + | + | + |
| B3 | L-fucose | − | − | − | − | − |
| B4 | D-galactose | + | + | + | + | + |
| B5 | gentiobiose | − | − | − | − | − |
| B6 | α-D-glucose | + | + | + | + | + |
| B7 | m-inositol | − | − | − | − | − |
| B8 | α-D-lactose | − | − | − | − | − |
| B9 | lactulose | − | − | − | − | − |
| B10 | maltose | + | + | + | + | + |
| B11 | D-mannitol | + | + | + | + | + |
| B12 | D-mannose | + | + | + | + | + |
| C1 | D-melibiose | − | − | − | − | − |
| C2 | β-methyl-D-glucoside | + | + | + | + | + |
| C3 | D-psicose | + | + | + | + | + |
| C4 | D-raffinose | − | − | − | − | − |
| C5 | L-rhamnose | − | − | − | − | − |
| C6 | D-sorbitol | + | + | + | + | + |
| C7 | sucrose | + | + | + | + | + |
| C8 | D-trehalose | + | + | + | + | + |
| C9 | turanose | | + | + | + | |
| C10 | xylitol | − | − | − | − | − |
| C11 | methyl-pyruvate | + | + | + | + | + |
| C12 | mono-methyl-succinate | + | + | + | + | + |
| D1 | acetic acid | + | + | + | + | + |
| D2 | cis-aconitic acid | − | − | − | − | − |
| D3 | citric acid | − | − | − | − | − |
| D4 | formic acid | − | − | − | | − |
| D5 | D-galactonic acid lactone | − | − | − | − | − |
| D6 | D-galacturonic acid | − | − | − | − | − |
| D7 | D-gluconic acid | + | + | + | + | + |
| D8 | D-glucosaminic acid | − | − | − | − | − |
| D9 | D-glucuronic acid | − | − | − | − | − |
| D10 | α-hydroxybutyric acid | − | − | − | − | − |
| D11 | β-hydroxybutyric acid | − | − | − | − | − |
| D12 | γ-hydroxybutyric acid | − | − | − | − | − |
| E1 | p-hydroxy-phenylacetic acid | − | − | − | − | − |
| E2 | itaconic acid | − | − | − | − | − |
| E3 | α-keto-butyric acid | − | − | − | − | − |
| E4 | α-keto-glutaric acid | − | − | − | | − |
| E5 | α-keto-valeric acid | + | − | − | − | + |
| E6 | D,L-lactic acid | − | − | − | − | − |
| E7 | malonic acid | − | − | − | − | − |
| E8 | propionic acid | − | − | | − | |
| E9 | quinic acid | − | − | − | − | − |
| E10 | D-saccharic acid | − | − | − | − | − |
| E11 | sebacic acid | − | − | − | − | − |
| E12 | succinic acid | + | + | + | + | + |
| F1 | bromo-succinic acid | + | + | + | + | + |
| F2 | succinamic acid | + | + | + | + | + |
| F3 | glucuronamide | − | − | − | − | − |
| F4 | alaninamide | + | + | + | + | + |
| F5 | D-alanine | + | + | + | + | + |
| F6 | L-alanine | + | + | + | + | + |
| F7 | L-alanyl-glycine | + | + | + | + | + |
| F8 | L-asparagine | + | + | + | + | + |
| F9 | L-aspartic acid | + | + | + | + | + |
| F10 | L-glutamic acid | + | + | + | + | + |
| F11 | glycyl-L-aspartic acid | + | + | + | + | + |
| F12 | glycyl-L-glutamic acid | + | + | + | + | + |
| G1 | L-histidine | | − | | | + |
| G2 | hydroxy-L-proline | − | − | − | − | − |
| G3 | L-leucine | − | − | − | − | − |
| G4 | L-ornithine | − | − | − | − | − |
| G5 | L-phenylalanine | − | − | − | − | − |
| G6 | L-proline | − | − | − | − | + |
| G7 | L-pyroglutamic acid | − | − | − | − | − |
| G8 | D-serine | + | + | + | + | + |
| G9 | L-serine | + | + | + | + | + |
| G10 | L-threonine | + | + | + | + | + |
| G11 | D,L-carnitine | − | − | − | − | − |
| G12 | γ-amino-butyric acid | − | − | − | − | − |
| H1 | urocanic acid | + | + | + | + | + |
| H2 | inosine | + | + | + | + | + |
| H3 | uridine | + | + | + | + | + |
| H4 | thymidine | + | + | + | + | + |
| H5 | phenyl-ethylamine | − | − | − | − | − |
| H6 | putrescine | − | − | − | − | − |
| H7 | 2-amino-ethanol | − | − | − | − | − |
| H8 | 2,3-butanediol | − | − | − | − | − |
| H9 | glycerol | + | + | + | + | + |
| H10 | D,L-α-glycerol phosphate | + | + | − | + | + |
| H11 | glucose-1-phosphate | + | + | + | + | + |
| H12 | glucose-6-phosphate | + | + | + | + | + |

The new isolates of Aeromonas can be distinguished by the following properties:

strain 1-does not utilize rhamnose, is resistant to DDPP at 150 μg/ml, is arginine dihydrolase negative, does not utilize 2-aminoethanol, does not oxidize L-proline.

strain 2-utilizes rhamnose, sensitive to DDPP at 150 μg/ml, more lytic activity for Xanthomonas (halo size) than strains 1, 4, 5 and 7.

strain 4-arginine hydrolysis, arginine dihydrolase positive, more amylase activity (halo size) than strains 1, 2, 5 and 7, less lytic activity for Xanthomonas (halo size) than strains 1, 2, 5 and 7.

strain 5-oxidizes 2-aminoethanol, less sensitive to 6% NaCl in LB broth.

strain 7-oxidizes L-proline.

strains 1, 5, 7 share an iridescent quality of colonies that is different from 2.

Strain 2 identified as strain B25 has been deposited on Feb. 26, 1992 in the name of Shin-Etsu Bio, Inc. with the American Type Culture Collection, 12301 Park Lawn Drive Rockville, Md. 20852, and assigned Deposit No. ATCC 55301. This deposit has been made pursuant to the provisions of the Budapest Treaty on the International recognition of the Deposit of Microorganisms for the Purposes of Patent Procedure and all restrictions of the availability to the public of the materials so deposited will be irrevocably removed upon the granting of a patent thereon.

EXAMPLE 3

Lysis of Xanthomonas Cells with the Inventive Enzyme

Agar plates were prepared which included (per liter): 100 ml 10x P2 salts, 15 g agar (Difco) and 100 ml heat-killed (2 hours at 90° C.) *Xanthomanas campestris* cells (Strain X74). The cells remained intact (not lysed) for the most part during heating. The 10x P2 salts included (per liter): 2 g $K_2HPO_4$, 1 g $(NH_4)_2HPO_4$, 0.5 g NaCl, 0.05 g $MgSO_4\text{-}7H_2O$ and 0.01 g each of $FeSO_4$, $MnSO_4$ and $ZnSO_4$.

Culture samples were spotted onto the agar plate and incubated at 30° C. for 3–4 days. Zones of clearing surrounding the colonies indicated that the surface cultures were secreting enzymes capable of lysing and digesting Xanthomanas cells and debris embedded in the agar. The radii of the visible clearing zones were measured from the centers of the growth zone. The results are set forth in Table 5.

TABLE 5

| Bacterial Isolate | Ratio of radius of clear zone to radius of growth zone |
|---|---|
| E. coli | (no clear zone) |
| P. aeruginosa | 2 (faint clear zone) |
| 1 | 2 |
| 2 | 2.5 |
| 4 | 1.2 |
| 5 | 2 |
| 7 | 2 |

EXAMPLE 4

Clarification of a Liquid Culture of Xanthomonas Cells and Xanthan Gum

*Xanthomonas campestris* strain X59 was grown in Luria broth with glucose at 3% (w/v) for 72 hours at 30° C. The xanthan accumulated in the broth had a concentration of 0.8% (w/v). The culture was then heated at 90° C. for 2 hours, and then stored at 4° C. for up to two weeks. Strain X59 has been deposited in the name of Shin-Etsu Bio, Inc. with the American Type Culture Collection, in Rockville, Md., and assigned Deposit No. ATCC 55298. This deposit has been made pursuant to the provisions of the Budapest Treaty on the International recognition of the Deposit of Microorganisms for the Purposes of Patent Procedure and all restrictions of the availability to the public of the materials so deposited will be irrevocably removed upon the granting of a patent thereon.

In addition, different species of Lysobacter were obtained from the American Type Culture Collection. It is generally recognized that variations in colony morphology arise in pure cultures of Lysobacter (P. Christensen and F. D. Cook, 1978, Lysobacter, a new genus of nonfruiting, gliding bacteria with a high base ratio. International Journal of Systematic Bacteriology 28: 367–393). Certain cultures received from the ATCC also showed the presence of more than a single colony type. The ATCC also noted that more than a single colony type were present. A culture identified as ATCC 27796 was obtained. This was known as *Lysobacter enzymogenes* subspecies *enzymogenes* (ibid.) Culture ATCC 27796 was cultured on standard YM agar plates. One isolate was obtained which formed opaque cream-colored colonies with irregular edges. This isolate was identified as B23. A second colony type appeared translucent with a regular circular edge. The B23 colony type produced the most lytic activity when assayed with heat-treated Xanthomonas cells, as compared to either the translucent variant or a mixture of the two types. The second colony type was not further studied. Strain B23 has been deposited in the name of Shin-Etsu Bio, Inc. on Apr. 22, 1992, with the American Type Culture Collection located at 12301 Park Lawn Drive, in Rockville, Md., 20852 and assigned Deposit No. ATCC 55319. This deposit has been made pursuant to the provisions of the Budapest Treaty on the International recognition of the Deposit of Microorganisms for the Purposes of Patent Procedure and all restrictions of the availability to the public of the materials so deposited will be irrevocably removed upon the granting of a patent thereon.

Cultures of *E. coli* as a non-enzyme producing comparison, new Aeromonas isolates 1 and 2 as described in Examples 1 and 2 above, *Lysobacter enzymogenes* (B23), and *Micropolyspora faeni* ATCC 21450, were cultured. *Lysobacter enzymogenes* and *Micropolyspora faeni* are known to produce enzymes that lyse bacteria. The strains were grown overnight in medium containing 0.5% Pharmamedia, 0.1% yeast extract (Difco), 0.2% $KH_2PO_4$, 0.05% $MgSO_4\text{-}7H_2$) and 1/10 volume of heat-inactivated (2 hours at 90° C.) *Xanthomonas campestris* strain X59. The cells were removed by centrifugation at about 6000× g for 10 minutes and the clarified culture supernatants stored at 4° C. Enzyme-producing test cultures were also prepared with M9 salts medium containing 0.2% w/v yeast extract and 1% w/v glucose. M9 salts contains per liter: 6 g $Na_2HPO_4$, 3 g $KH_2PO_4$, 0.5 g NaCl, 1 g $NH_4Cl$, 10 ml of a 0.01M solution of $CaCl_2$ and 1 ml of a 1M solution of $MgSO_4\text{-}7H_2O$ (the latter two components are added after autoclaving). The Micropolyspora strain was grown at 45° C. and the others were grown at 30° C.

The heat-killed Xanthomonas culture was diluted with four volumes of water and then 5 ml were mixed with 0.2 ml of enzyme-containing culture supernatant. After incubation for 24 or 48 hours at 40° C., optical densities were measured at 600 nm. The results are shown in Table 6.

TABLE 6

| | Optical Density | |
|---|---|---|
| Bacterial Strain | 24 hours digest* | 48 hour digest** |
| E. coli | 0.54 | 0.79 |
| Aeromonas 1 | 0.46 | 0.62 |
| Aeromonas 2 | 0.46 | 0.59 |
| M. faeni | 0.35 | 0.50 |
| L. enzymogenes | 0.23 | 0.46 |

*Reactions were diluted 1:10 before measurement
**Reactions were diluted 1:4 before measurement

EXAMPLE 6

Effect of Enzymatic Clarification on Xanthan Polysaccharides

*Xanthomonas campestris* strain X59 was grown in YM medium containing 2% w/v glucose for 20 hours at 30° C. The optical density at 600 nm reached 1.3. The culture was heat treated at 75° C. for 60 min and then cooled and stored for up to a week at 4° C. The optical density at 600 nm after heat treatment was 0.92 and the pH was 7.9. Samples of 10 g were weighed into screw-capped polypropylene tubes. Three samples received 0.1 ml of deionized water and three received 0.1 ml of a cell-free supernatant of a culture of *Lysobacter enzymogenes* B23. The *Lysobacter enzym.* used was obtained by growing B23 overnight at 30° C. in liquid M9 medium containing 0.2% w/v yeast extract and 1% w/v glucose, and then centrifuging to remove the cells. To determine the clarity of the heat-treated Xanthomonas culture, the optical densities at 600 nm were measured. The samples were incubated at 50° for four hours. Each sample was then precipitated with 2 volumes of IPA and the precipitated xanthan was pressed and dried overnight at 80° C. The dry xanthan was weighed and redissolved in deionized water at a final concentration of 0.30% w/v and the optical densities at 600 nm measured. The results are set forth in Table 7.

TABLE 7

| Sample | | Optical density 4 hr | 6 hr* | Weight of precipitate (mg) | Optical density of re-suspended xanthan |
|---|---|---|---|---|---|
| No | 1 | 0.85 | — | 31 | 1.23 |
| Enzymes | 2 | 0.86 | — | 34 | 1.28 |
| | 3 | 0.81 | — | 34 | 1.26 |
| Lysobacter | 1 | 0.58 | — | 29 | 0.83 |
| enzymogenes | 2 | 0.48 | — | 29 | 0.78 |
| | 3 | 0.50 | 0.19 | 26 | 0.28 |

*Sample received 0.4 ml additional enzyme extract and an additional 2 hours at 50° C.

Viscosities of each of the samples were measured with a Brookfield LVTDV-II viscometer using a small sampler spindle (number 18) for which the shear rate equals 1.22 times the spindle rpm and tabulated in Table 8. As shown, the viscosity of the xanthan was not reduced by incubation of xanthan-containing cultures with the cell-free supernatants from *Lysobacter enzymogenes* B23. This means that the enzymes present in the supernatant do not adversely affect the xanthan polysaccharide by degrading it, i.e., by hydrolyzing it.

TABLE 8

| | Viscosities (cp) | | | | | |
|---|---|---|---|---|---|---|
| | No enzyme samples | | | Lysobacter samples | | |
| RPM | 1 | 2 | 3 | 1 | 2 | 3 |
| 60 | 31 | 32 | 31 | 31 | 32 | 34 |
| 30 | 52 | 54 | 53 | 55 | 56 | 59 |
| 12 | 107 | 107 | 105 | 108 | 110 | 120 |
| 6 | 194 | 191 | 187 | 197 | 202 | 220 |

EXAMPLE 7

*Lysobacter enzymogenes* (B23) was cultured in various growth media to identify medium components that promote the synthesis and secretion of bacteriolytic enzymatic activities into the culture broth from the cells. After 28 and 48 hours of growth at 30° C., the Lysobacter cells were removed by centrifugation and the cell-free culture broths were tested for their ability to clarify suspensions of heat-treated Xanthomonas cells. A culture of Xanthomonas was grown in YM broth and then incubated at 70° C. for 90 minutes. After heat treatment, the pH was about 9 and the absorbance at 600 nm was about 0.9 to 1.0. In each test, 0.1 ml of the culture supernatants were added to 4.0 ml of heat-treated Xanthomonas cells. After specified durations of incubation at 55° C., the absorbance at 600 nm was measured. The reaction mixtures were shaken immediately after mixing and then before each absorbance measurement. The media are as follows (weight of component per liter of final volume:

YM includes 3 g yeast extract (Difco), 3 g malt extract (Difco) and 10 g glucose; 5 g peptone (Difco); cells (Xc) were heat-killed *Xanthomonas campestris*; whey was permeate from Land O'Lakes;

SP-4 protease (from Nagase Company) is a powder containing about 4% by weight as an alkaline protease. The final concentration of the alkaline protease in the test was 20 ppm of enzyme.

The results are tabulated in Table 9.

TABLE 9

| | Absorbance (600 nm) Lysobacter culture time (hr) | | | | | |
|---|---|---|---|---|---|---|
| | 28 | | | 48 | | |
| | Enzyme reaction time (min) | | | | | |
| Enzyme sample | 10 | 60 | 180 | 10 | 60 | 180 |
| No enzyme control | 0.94 | 0.94 | 0.94 | 0.93 | 0.93 | 0.93 |
| Protease SP-4 | 0.42 | 0.24 | 0.18 | 0.42 | 0.24 | 0.18 |
| Lysobacter culture medium*) | | | | | | |
| YM | 0.71 | 0.32 | 0.19 | 0.64 | 0.13 | 0.07 |
| YM − glucose | 0.79 | 0.49 | 0.31 | 0.76 | 0.35 | 0.20 |
| YM − yeast extract | 0.89 | 0.79 | 0.77 | 0.90 | 0.79 | 0.76 |
| YM − malt extract | 0.66 | 0.21 | 0.13 | 0.53 | 0.08 | 0.05 |
| YM − peptone | 0.74 | 0.49 | 0.33 | 0.78 | 0.54 | 0.34 |
| YM − glucose + cells (Xc) | 0.71 | 0.36 | 0.23 | 0.78 | 0.47 | 0.28 |
| Glucose + cells (Xc) | 0.88 | 0.82 | 0.75 | 0.87 | 0.78 | 0.72 |
| Cells (Xc) | 0.89 | 0.84 | 0.77 | 0.88 | 0.83 | 0.76 |
| Casamino Acids | 0.88 | 0.88 | 0.88 | 0.91 | 0.89 | 0.86 |
| Tryptone | 0.86 | 0.70 | 0.60 | 0.87 | 0.73 | 0.62 |
| Whey | 0.90 | 0.86 | 0.80 | 0.89 | 0.85 | 0.79 |
| Yeast nitrogen base | 0.93 | 0.88 | 0.86 | 0.91 | 0.88 | 0.84 |
| M9 salts + glucose | 0.88 | 0.78 | 0.72 | 0.87 | 0.76 | 0.68 |

*) a − (minus) means the following component was not present, a + (plus) means the following component was present.

A low absorbance at 600 nm indicates that more lysis and clarification occurred. As shown, Lysobacter grown in YM lacking malt extract produced the most clarification activity. YM medium is a rich source of nutrients, including yeast extract, malt extract, peptone and glucose. The results show that certain components in YM medium can be eliminated and still allow the accumulation of lytic activity in the culture supernatants. To obtain a high yield of lytic enzymes, it is preferable to include yeast extract (vitamins and amino acids) and glucose (carbon source). It is not important to attempt to induce the synthesis by including the substrate Xanthomonas cells or whole proteins, such as, casein, in the culture medium.

EXAMPLE 8

Xanthan gum (Keltrol TM from Kelco Company, San Diego, Calif.) was dissolved in deionized water at final concentrations of 0.5 and 2.0% (w/v). Welan gum (K1A96 from Kelco Company) was similarly prepared at 1% (w/v). Each of the three samples was divided into two equal parts. To one part of each sample was added 0.5 ml of enzyme prepared from a culture of Lysobacter strain B23. There was no addition to the control part of each sample. To obtain the enzyme, Lysobacter strain B23 was grown in liquid medium in a flask with shaking at 30° C. for 60 hours. The medium included 3 g yeast extract (Difco), 2 g Bacto peptone (Difco), 3 g glucose and 2 g $KH_2PO_4$ per liter of deionized water, and had an initial pH of about 6.1. Sodium azide was added to the 2% xanthan gum samples to 0.01% (w/v) to prevent bacterial growth. The 2% xanthan gum samples were mixed at room temperature (20°-24° C.) by repeated inversion on a wheel rotating at about 5–10 rpm. The 0.5% xanthan gum and 1% welan samples were incubated at 55° C. without mixing, but are inverted by hand about 5 to 10 times immediately prior to sampling for measurements of transparency. An additional increment (0.5 ml) of the same enzyme preparation was added to the 1.0% welan sample at 2.25 hr. Similarly, an additional 0.5 ml of the same enzyme preparation was added to the 0.5% xanthan gum sample at 3.25 hr. At 17.25 hr, an additional 1.0 ml of the same enzyme was added to the 1% welan sample along with sodium azide to a final concentration of 0.01% (w/v), and the mixture was shifted to room temperature and mixed by inversion on the rotating wheel as above. At the times indicated in the Table 9, percent transparency was measured at 600 nm for a 1 cm light path, with deionized water serving as a 100% transparent standard. The transparency for each of the enzyme-treated samples increased. Thus, the enzyme from Lysobacter strain B23 can clarify solutions of polysaccharide gums that were previously exposed to isopropylalcohol as part of the process of precipitating the polysaccharide from fermentation broths.

TABLE 10

| Time (hr) | 0.5% xanthan gum | | 2% xanthan gum | | 1% Welan | |
|---|---|---|---|---|---|---|
| | +enzyme | control | +enzyme | control | +enzyme | control |
| 0 | ND* | 34 | ND | 3 | ND | 2 |
| 1 | 75 | 33 | ND | ND | ND | ND |
| 2 | 83 | 35 | ND | ND | 6 | 2 |
| 3 | 85 | 33 | ND | ND | ND | ND |
| 17 | ND | ND | ND | ND | 9 | 3 |
| 18 | 87 | 40 | ND | ND | ND | ND |
| 41 | ND | ND | ND | ND | 9 | 2 |
| 43 | ND | ND | 14 | 3 | ND | ND |
| 65 | ND | ND | ND | ND | 8 | 3 |
| 67 | ND | ND | 20 | 3 | ND | ND |

*ND indicates no determination

In addition, at 67 hours, the 2% xanthan gum samples were diluted with deionized water to 1% and 0.5% final concentrations and transparencies were measured. The enzyme treated and diluted samples (1% and 0.5%) were 63% and 82% transparent, respectively. The corresponding untreated and diluted samples (1% and 0.5%) were 15% and 40% transparent.

The treated and untreated samples were tested for viscosity per gram in order to see whether or not the enzyme and heat treatments caused degradation of the polymers. First, the 2% xanthan gum samples were diluted to 1% (w/v) with deionized water and then the viscosities were measured at 22° C. at various shear rates using spindle 4 and an LVTDV-II Brookfield viscometer. The results are shown in Table 11 and indicate that enzyme treatment of xanthan gum at 20°-24° C. for as long as 67 hours does not degrade the polymer, since the final viscosities are at least as high as the viscosities of the untreated control.

TABLE 11

| Shear rate ($sec^{-1}$) | +Enzyme | Control |
|---|---|---|
| 12.54 | 1040 | 972 |
| 6.27 | 1700 | 1640 |
| 2.51 | 3900 | 3540 |
| 1.25 | 7550 | 6700 |
| 0.63 | 13600 | 12500 |

EXAMPLE 9

Lysis of Different Bacterial Species

Christensen and Cook (Int. J. Syst. Bact. 28: 367–393, 1978) rated various Lysobacter species for their ability to lyse different types of microbial cells that were growing on the surface of nutrient agar plates. They classified the extent of lysis as either "good", "possible" or "none". Of the cells tested, Escherichia coli, Arthrobacter sp., Bacillus subtilis, two actinomycetes (UASM 4432 and UASM 4441), Rhizopus sp., Penicillium notatum, Sclerotinia sclerotiorum, yeast, and Chlorella sp. showed "good" lysis. Serratia marcescens was "not" lysed and Pseudomonas aeruginosa was "possibly" lysed. Each of 46 strains of Lysobacter sp. tested showed "good" lysis of at least some of the above listed growing microbial cells. One of the strains tested was Lysobacter enzymogenes (ATCC 27796).

It is desirable to be able to quickly and simply determine a method for predicting whether compounds secreted by an organism, e.g., strain B23 could lyse an untested microorganism, since each bacterial genus usually has a unique cell wall structure and chemistry.

As shown in Example 3 hereof, strain B23 secretes lytic compounds into the cell culture medium that exhibit useful lytic activity towards Xanthomonas campestris strain X59. In order to quickly and easily determine the lytic activity of a given organism, e.g., Lysobacter, with respect to other bacterial species, the following procedure was used: A solidified test medium containing heat-killed cells and cellular debris of the particular bacterial species to be tested e.g., an agar gel. The strain, the lytic activity of which is to be tested, is subjected to growth conditions on the solidified test medium. Digestion of the cellular material causes a visible zone of clearing around the circular spot of growing cells, if the strain produces a lytic enzyme.

I have quantified the lytic activity by determining the amount of clearing resulting from the production of lytic enzymes. This is done by measuring the area or diameter of the circular zone of clearing and the area or diameter of the zone of cell growth and then calculating the ratio of the diameter of clearing to the diameter of growth. The higher this ratio, the greater is the lytic activity of the strain being tested under the particular growth conditions used.

In this example, this test is used to measure the lytic activity of strain B23 towards a number of bacterial species commonly used by industrial microbiologists to produce exopolysaccharides and proteins, including products of recombinant DNA technology.

For strain B23, the clearing zones are visible within about 16 hours of incubation at 30° C., although this depends on the concentration of Lysobacter cells initially spotted onto the medium. The zones expand radially over the succeeding 48 hours. The measurement can be made at any time after the zone of clearing becomes visible. For this example, the agar plates containing cellular debris were prepared by growing each microorganism to saturation in LB medium (10 g Bacto tryptone, Difco, 5 g Bacto yeast extract, Difco, and 10 g NaCl per liter of deionized water), heating the culture at 80° C. for 60 minutes, and then adding 9 volumes of M9 medium containing 0.1% w/v glucose and 20% agar (Difco). The M9 medium included, per liter of deionized water, 6 g $Na_2HPO_4$, 3 g $KH_2PO_4$, 0.5 g NaCl, 1 g $NH_4Cl$ and after sterilization, 10 ml of sterile 0.01M $CaCl_2$ solution and 1 ml of sterile 1M $MgSO_4$-$7H_2O$ were added. The Lysobacter cultures were grown to saturation in M9 minimal salts medium containing 0.5% (w/v) yeast extract and trace minerals for about 16 hours at 30° C.

The names and ATCC numbers for the Lysobacter strains were as follows:

B23, *Lysobacter enzymogenes* ATCC 55319;
B48, *Lysobacter gummosus* ATCC 29489;
B49, *Lysobacter brunescens* ATCC 29482;
B50, *Lysobacter brunescens* ATCC 29483;
B51, *Lysobacter brunescens* ATCC 29484; and
B52, *Lysobacter enzymogenes* subspecies *cookii* ATCC 29488.

Table 11 shows the amounts of clearing for each bacterial species incorporated into the solid M9 medium.

TABLE 11

| Bacterial Species | ATCC Number | Amount of Clearing* | | | | | |
|---|---|---|---|---|---|---|---|
| | | B23 | B52 | B48 | B49 | B50 | B51 |
| Xanthomonas campestris | 55298 | 1.6 | 1.6 | 1.6 | 1.0 | 1.0 | 1.0 |
| Pseudomonas aeruginosa | 27853 | 1.3 | 1.6 | 1.2 | 1.0 | 1.0 | 1.0 |
| Arthobacter viscosus | 19584 | 1.6 | 1.8 | 1.2 | 1.0 | 1.0 | 1.0 |
| Escherichia coli | 53323 | 1.5 | 1.9 | 1.3 | 1.0 | 1.0 | 1.0 |
| Pseudomonas sp. | 31554 | 2.0 | 2.3 | 1.3 | 1.0 | 1.0 | 1.0 |
| Pseudomonas elodea | 31461 | 1.3 | 1.8 | 1.3 | 1.0 | 1.0 | 1.0 |
| Alcaligenes sp. | 31555 | 1.7 | 2.5 | 1.3 | 1.0 | 1.0 | 1.0 |
| Klebsiella pneumoniae | 12657 | 1.4 | 1.8 | 1.1 | 1.0 | 1.0 | 1.0 |
| Beijerinckia indica | 21423 | 2.0 | 2.5 | 1.6 | 1.0 | 1.0 | 1.0 |
| Agrobacterium radiobacter | 31643 | 1.0 | 1.0 | 1.0 | 1.0 | 1.0 | 1.0 |
| Alcaligenes sp. | 31853 | 1.4 | 2.0 | 1.3 | 1.0 | 1.0 | 1.0 |
| Alcaligenes sp. | 31961 | 1.7 | 2.0 | 1.5 | 1.0 | 1.0 | 1.0 |
| Bacillus subtilis W168 | — | 1.6 | 1.2 | 1.3 | 1.0 | 1.0 | 1.0 |

*The Amount of Clearing is the ratio of the diameter of the zone of clearing to the diameter of the zone of growth. The value 1.0 indicates no clearing zone. One standard deviation on replicate measurements was less than ±0.1.

It is thus clear that Lysobacter strain B23 can be used to clarify polysaccharide-containing cultures of a variety of microbial species. These results also show that other Lysobacter species are capable of secreting compounds that can be used to lyse these bacteria.

EXAMPLE 10

A series of experiments were carried out to examine the conditions which effect production of lytic enzymes by bacteria.

Experiment 10A

Media for Production of the Lysobacter B23 Lytic Compounds

A "seed" culture of Lysobacter strain B23 was grown in a triple-baffled flask of 125 ml capacity in 25 ml of YM medium without glucose for 44 hours at 30° to 32° C. with rotary shaking at 210 rpm. YM medium included per liter of deionized water: 3 g yeast extract, 3 g malt extract, 5 g peptone, and 10 g glucose. The inoculum for the seed culture was about 5-25 microliters and was taken directly from a colony of cells growing on the surface of an agar plate containing YM medium after 3 days of growth at 30° C. and storage at 4° C. for 12 days. After 44 hours of growth, the pH of the culture reached about 8 and the absorbance of the culture at 600 nm (A600) was about 4. Portions of the seed culture were then used to inoculate 25 ml of each of several "medium test" cultures in triple-baffled flasks of 125 ml capacity at a ratio of 1.0% (v/v).

The media components, concentrations and results of the clarifications are set forth in Table 13.

In Table 13, the following abbreviations are used:
Yex = yeast extract;
Pep = peptone;
Glc = glucose;
KHP = $KH_2PO_4$;
Dby = dried brewer's yeast; and
Mex = malt extract.

The "medium test" cultures were grown for 40 hours at 28° to 32° C. with shaking at 210 rpm. The initial pH values ranged from 6.05 to 6.22. The lytic compounds were purified from each culture broth by centrifugation at 10,000× gravity for 15 min. The supernatant was retained and the cell pellet was discarded.

The purified lytic compounds were assayed for clarification activity by measuring the decrease in A600 of a sample of heat-treated substrate cells. The substrate cells were prepared by growing *Xanthomonas campestris* Strain X83 in YM without glucose to a final A600 of about 1.1 and then heating the culture at 70° C. for 90 min to kill the cells. Strain X83 is defective in accumulation of xanthan and therefore the culture broth does not become viscous. The mutant strain was used to enable more efficient mixing of the lytic enzymes and the substrate cells. The A600 of the substrate at the start of each assay was 0.97. The assays were incubated at 55° C. and samples were analyzed at A600 for incubation times of 10, 60, 180 and 360 minutes.

The results indicate that a variety of media will support the growth of Lysobacter and lead to the accumulation in the medium of lytic compounds. Judging by the amount of lytic activity, the best combinations of components are given in media 2, 4 and 13.

TABLE 13

| Medium | | | | | | | | | A600 | | | |
|---|---|---|---|---|---|---|---|---|---|---|---|---|
| Concentration (g/l) of Medium Component | | | | | | | | | Duration of assay (min) | | | |
| No. | YEx | Pep | Glc | KHP | Dby | MEx | Final pH | Final A600 | 10 | 60 | 180 | 360 |
| 1 | 3 | 2 | 3 | 0 | 0 | 0 | 8.7 | 0.8 | 0.84 | 0.83 | 0.79 | 0.76 |
| 2 | 3 | 2 | 3 | 2 | 0 | 0 | 8.1 | 1.5 | 0.57 | 0.18 | 0.11 | 0.09 |
| 3 | 3 | 0 | 3 | 0 | 0 | 0 | 8.2 | 1.2 | 0.72 | 0.55 | 0.37 | 0.23 |
| 4 | 3 | 0 | 3 | 2 | 0 | 0 | 7.1 | 2.6 | 0.63 | 0.21 | 0.11 | 0.09 |

TABLE 13-continued

| | Medium | | | | | | | | A600 | | | |
|---|---|---|---|---|---|---|---|---|---|---|---|---|
| Concentration (g/l) of Medium Component | | | | | | | | | Duration of assay (min) | | | |
| No. | YEx | Pep | Glc | KHP | Dby | MEx | Final pH | Final A600 | 10 | 60 | 180 | 360 |
| 5 | 0 | 0 | 3 | 0 | 3 | 0 | 7.1 | 3.3 | 0.72 | 0.52 | 0.36 | 0.24 |
| 6 | 0 | 0 | 3 | 2 | 3 | 0 | 6.2 | 3.4 | 0.80 | 0.66 | 0.56 | 0.48 |
| 7 | 1 | 0 | 3 | 0 | 2 | 0 | 7.2 | 3.4 | 0.74 | 0.51 | 0.33 | 0.24 |
| 8 | 1 | 0 | 3 | 2 | 2 | 0 | 6.7 | 2.7 | 0.74 | 0.54 | 0.37 | 0.27 |
| 9 | 2 | 0 | 3 | 0 | 1 | 0 | 7.7 | 3.0 | 0.70 | 0.48 | 0.30 | 0.20 |
| 10 | 2 | 0 | 3 | 2 | 1 | 0 | 6.9 | 2.1 | 0.66 | 0.31 | 0.19 | 0.15 |
| 11 | 3 | 0 | 0 | 0 | 0 | 0 | 8.8 | 0.7 | 0.73 | 0.57 | 0.41 | 0.29 |
| 12 | 0 | 0 | 0 | 0 | 3 | 0 | 8.6 | 1.1 | 0.74 | 0.57 | 0.41 | 0.28 |
| 13 | 3 | 3 | 0 | 0 | 0 | 5 | 9.0 | 2.6 | 0.61 | 0.21 | 0.10 | 0.08 |

Experiment 10B
Initial pH of Medium for Production of Lytic Compounds from Lysobacter A "seed" culture of Lysobacter strain B23 was grown in a triple-baffled flask of 125 ml capacity in 25 ml of YM medium without glucose for 44 hours at 30° to 32° C. with rotary shaking at 210 rpm. YM medium without glucose contained per liter of deionized water: 3 g yeast extract, 3 g malt extract and 5 g peptone. The inoculum for the seed culture was about 5–25 microliters and was taken directly from a colony of cells growing on the surface of an agar plate containing YM medium after about 2 days of growth at 30° C. Portions of the seed culture were then used to inoculate 25 ml of each of three "pH test" cultures in triple-baffled flasks of 125 ml capacity at a ratio of 4% (v/v). Before inoculation, the medium in the three flasks was adjusted to a pH of 6, 7, or 8. There was one culture at pH 6, one at pH 7, and one at pH 8. The medium contained per liter of deionized water: 3 g yeast extract, 5 g peptone and 10 g glucose. The lytic compounds were purified from each culture broth by centrifugation at 10,000× gravity for 15 min. The supernatant was retained and the cell pellet was discarded.

The purified lytic compounds were assayed for clarification activity by measuring the decrease in A600 of a sample of heat-treated substrate cells. The substrate cells were prepared by growing *Xanthomonas campestris* strain X83 in YM without glucose to a final A600 of about 1 and then heating the culture at 70° C. for 90 min to kill the cells. The pH of the heat-treated culture was about 9. Each reaction mix contained 4 ml heat-treated substrate and 1 ml of test sample made up in deionized water. The initial A600 of the substrate at the start of each assay was 0.89. The assays were incubated at 55° C. and sampled for A600 at 10, 60, 180 and 360 min. The pH of the assay during the procedure was 9.

As a comparison, a sample of the protease SP-4 was also tested. SP-4 is a powder containing 4% (w/w) of alkaline protease prepared from a Bacillus species, 20% (w/w) $CaCO_3$, and 76% (w/w) of an absorbent (product of Nagase Company of Japan). The SP-4 enzyme was prepared by resuspending the crude powder in deionized water at 10,000 ppm (as powder). The enzyme is soluble at this level, however, the absorbent is insoluble. The SP-4 solution was centrifuged to precipitate the insoluble material and the clear supernatant containing the enzyme was retained and stored at 4° C. until use. The results of the clarification assays are shown in Table 14. In Table 14, 500 ppm of SP-4 refers to the crude powder of which the enzyme is 4% by weight.

TABLE 14

| Lysobacter B23 Initial pH of Lysobacter culture | A600 Duration of assay (min) | | | |
|---|---|---|---|---|
| | 10 | 60 | 180 | 360 |
| 6.0 | 0.56 | 0.16 | 0.10 | 0.06 |
| 7.0 | 0.67 | 0.27 | 0.12 | 0.10 |
| 8.0 | 0.69 | 0.33 | 0.15 | 0.11 |
| SP-4 powder (500 ppm) (20 ppm of enzyme) | 0.45 | 0.24 | 0.14 | 0.12 |

The results show that clarification compounds are more abundant in cultures of Lysobacter when the initial pH of the growth medium is 6. Also, the lytic activity in the Lysobacter cultures was seen to be at least as potent for clarifying Xanthomonas cultures as SP-4 powder used at 500 ppm.

Experiment 10C
Inoculum Size for Producing the Lysobacter Compounds for Clarification of Xanthomonas cells and Cell Debris A "seed" culture of Lysobacter strain B23 was grown in a triple-baffled flask of 500 ml capacity in 100 ml of YM medium for 48 hours at 30° to 32° C. with rotary shaking at 230 rpm. YM medium included per liter of deionized water: 3 g yeast extract, 3 g malt extract, 5 g peptone, and 10 g glucose. The inoculum for the seed culture was about 5–25 microliters and was taken directly from a colony of cells growing on the surface of an agar plate containing YM medium after 2–7 days of growth at 30° C. The initial pH of the culture was 6.0, and the final pH was between 7 and 8. The A600 of the culture was between 2 and 3.

Portions of the seed culture were then used to inoculate 100 ml of each of three "production" cultures in triple-baffled flasks of 500 ml capacity at an inoculation ratio of either 0.2, 1.0 or 5.0% (v/v). The production medium included per liter of deionized water: 3 g yeast extract, 2 g peptone, 3 g glucose and 2 g $KH_2PO_4$. The production culture was grown for 56 hours at 28° to 32° C. with shaking at 230 rpm. The initial pH was 6, and then gradually increased naturally over 56 hours to about 8. The culture times required to reach the highest culture densities, i.e., the highest A600, for the cultures inoculated at 0.2, 1.0, or 5.0% (v/v) were about 40, 32, and 28 hours, respectively. The peak A600 values were about 4 to 5. However, in each case, the A600 values observed at 48 and 56 hours were lower than the peak values, and were in the range of from 2 to 3. The lytic compounds were purified by removing the cells by centrifugation for about 15 minutes at about 10,000× gravity.

The purified lytic compounds were assayed for clarification activity by measuring the decrease in A600 of a sample of heat-treated substrate cells. The substrate cells were prepared by growing *Xanthomonas campestris* strain X83 in YM without glucose to a final A600 of about 1.1 and then heating the culture at 70° C. for 90 min to kill the cells. The initial A600 analysis of the substrate at the start of each assay was 0.87. The assays were incubated at 45° C. and sampled for A600 at 15, 60 and 180 minutes. The results of the clarification assays are shown in Table 15 for samples of lytic compounds harvested from cultures from each inoculum at 12, 24 and 32 hours.

The greatest amount of activity was obtained with the 5.0% inoculum, as seen by the reductions in A600 found in the shortest assay period (15 min). An inoculum size greater than 5% will also result in accumulation of the lytic compounds. The results show that the inoculum size for a production culture can be as low as 0.2%. However, a longer culture time is required to produce an equivalent amount of the lytic activity.

TABLE 15

| Inoculum size (%) | Harvest time (hr) | A600 Incubation Period (min) | | Assay 180 |
|---|---|---|---|---|
| | | 15 | 60 | |
| 0.2 | 12 | 0.87 | 0.87 | 0.87 |
| | 24 | 0.82 | 0.69 | 0.47 |
| | 32 | 0.39 | 0.11 | 0.05 |
| | 48 | 0.40 | 0.08 | 0.05 |
| | 56 | 0.39 | 0.15 | 0.05 |
| 1.0 | 12 | 0.87 | 0.87 | 0.87 |
| | 24 | 0.47 | 0.12 | 0.05 |
| | 32 | 0.40 | 0.10 | 0.05 |
| | 48 | 0.42 | 0.08 | 0.05 |
| | 56 | 0.43 | 0.08 | 0.05 |
| 5.0 | 12 | 0.85 | 0.78 | 0.75 |
| | 24 | 0.31 | 0.07 | 0.05 |
| | 32 | 0.31 | 0.07 | 0.05 |
| | 48 | 0.32 | 0.07 | 0.05 |
| | 56 | 0.34 | 0.09 | 0.05 |

Experiment 10D

Production of Lytic Compounds by Culturing Lysobacter B23 in a Stirred Jar Fermenter A "seed" culture of Lysobacter strain B23 was grown in a triple-baffled flask of 500 ml capacity in 100 ml of YM medium for 60 hours at 30° to 32° C. with rotary shaking at 210 rpm. YM medium includes per liter of deionized water: 3 g yeast extract, 3 g malt extract, 5 g peptone and 10 g glucose. The inoculum for the seed culture was about 5–25 microliters and was taken directly from a colony of cells growing on the surface of an agar plate containing YM medium after about 3 days of growth at 30° C. A portion of the seed culture was then used to inoculate a jar fermenter containing 4 liters of YPGP medium which included per liter of deionized water: 3 g yeast extract, 2 g peptone, 3 g glucose and 2 g $KH_2PO_4$. The initial pH was 6.2. Organic antifoam 204 from Sigma (AF) was diluted to 33% (v/v) with water. Less than 10 ml were automatically added to the fermenter to control foaming during the fermentation. The initial A600 of the culture was 0.2 and increased for 24 hours to about 4 and then decreased to about 1 at 48 hours when the culture was harvested. The pH increased gradually to around 8–9. Another portion of the seed culture was used to inoculate two cultures in triple-baffled 500 ml flasks at the same final cell density and containing 100 ml of the same medium, except that one flask included antifoam (0.1 ml of 33% v/v antifoam 204) and one flask did not contain antifoam. The flasks were incubated at 30° C. with rotary shaking at 210 rpm. The lytic compounds were purified from the culture broths by centrifugation at 10,000× gravity for 15 minutes. The supernatants were retained and the cell pellets were discarded.

The purified lytic compounds were assayed for clarification activity by measuring the decrease in A600 of a sample of heat-treated substrate cells. The substrate cells were prepared by growing *Xanthomonas campestris* strain X83 in YM without glucose to a final A600 of about 1 and then heating the culture at 70° C. for 90 minutes to kill the cells. The pH of the heat-treated culture was about 9. Each reaction mix contained 4 ml of heat-treated substrate and 1 ml of test sample made up in deionized water. The initial A600 of the substrate at the start of each assay was 0.85. The assays were incubated at 45° C. and analyzed for A600 at 15, 60 and 180 minutes of incubation time. The pH of the assay was 9.

A test was also conducted to determine whether or not the antifoam itself would inhibit the clarification activity if added to the reaction assay. Antifoam was added to a portion of the 30 hour sample from the culture grown in the absence of antifoam. The amount of antifoam added to the assay was equal to the amount of antifoam that would be introduced into an assay if the culture being tested had initially included antifoam. A comparative test was also carried out with the alkaline protease Nagase SP-4 as prepared in Experiment 10B.

The results are set forth in Table 16 and show that the lytic compounds can be prepared in a stirred jar fermenter as well as in a shaking flasks. The results also indicate that the inclusion of antifoam has a relatively small, but measurable detrimental effect on the accumulation of the lytic activities. However, addition of antifoam to a reaction assay does not reduce the amount of lytic activity (see the fourth of five data sets in the Table 16).

TABLE 16

| Culture tested | Time (hr) | A600 Duration of assay (min) | | |
|---|---|---|---|---|
| | | 15 | 60 | 180 |
| Jar fermenter + AF | 0 | 0.81 | 0.75 | 0.63 |
| | 6 | 0.81 | 0.73 | 0.62 |
| | 12 | 0.79 | 0.68 | 0.45 |
| | 24 | 0.41 | 0.05 | 0.03 |
| | 30 | 0.34 | 0.05 | 0.03 |
| | 36 | 0.34 | 0.06 | 0.03 |
| | 48 | 0.35 | 0.06 | 0.03 |
| Flask + AF | 6 | 0.84 | 0.73 | 0.60 |
| | 12 | 0.78 | 0.64 | 0.36 |
| | 24 | 0.33 | 0.06 | 0.03 |
| | 30 | 0.31 | 0.06 | 0.03 |
| | 36 | 0.33 | 0.07 | 0.03 |
| | 48 | 0.34 | 0.07 | 0.04 |
| Flask (No AF) | 6 | 0.81 | 0.74 | 0.57 |
| | 12 | 0.78 | 0.66 | 0.39 |
| | 24 | 0.25 | 0.06 | 0.04 |
| | 30 | 0.23 | 0.05 | 0.04 |
| | 36 | 0.25 | 0.05 | 0.04 |
| | 48 | 0.26 | 0.06 | 0.04 |
| Flask (No AF) (AF added to assay) | 30 | 0.25 | 0.05 | 0.03 |
| Nagase SP-4 (500 ppm) | | 0.19 | 0.11 | 0.10 |

Experiment 10E

Stability of the Lytic Activity to Temperature and pH

A sample of Lysobacter B23 lytic compound was prepared as described in Experiment 10D. This was divided into smaller samples and each was treated for 1 or 3 hours at various temperatures or pH values, and then assayed as in Experiment 10D, except that the initial A600 value of the substrate heat-treated Xanthomonas cells was 0.88 and the assay was incubated at 55° C. for 60 or 180 minutes. The pH was adjusted by adding HCl or NaOH. One volume of B23 lytic compound was mixed with 40 volumes of substrate cells for a total assay volume of 4–5 ml. Table 17 shows the effects of the pretreatments on the clarification activity.

The results indicate that the activity of the lytic compounds is stable at or below about 37° C. and unstable at or above about 55° C. The lytic activity was stable from about pH 7 to 11.

TABLE 17

| Pretreatment | | A600 Assay duration (min) | |
|---|---|---|---|
| Condition | Time (hr) | 60 | 180 |
| Temperature (°C.) | | | |
| 4 | 1 | 0.12 | 0.06 |
| 4 | 3 | 0.12 | 0.06 |
| 23 | 1 | 0.12 | 0 05 |
| 23 | 3 | 0.13 | 0.06 |
| 30 | 1 | 0.12 | 0.05 |
| 30 | 3 | 0.12 | 0.07 |
| 37 | 1 | 0.12 | 0.05 |
| 37 | 3 | 0.10 | 0.05 |
| 55 | 1 | 0.47 | 0.29 |
| 55 | 3 | 0.66 | 0.49 |
| 66 | 1 | 0.79 | 0.72 |
| 66 | 3 | 0.86 | 0.86 |
| pH | | | |
| 7 | 1 | 0.13 | 0.06 |
| 7 | 3 | 0.14 | 0.07 |
| 8 | 1 | 0.11 | 0.05 |
| 8 | 3 | 0.13 | 0.06 |
| 8.5 | 1 | 0.13 | 0.06 |
| 8.5 | 3 | 0.13 | 0.06 |
| 9 | 1 | 0.13 | 0.06 |
| 9 | 3 | 0.14 | 0.06 |
| 10 | 1 | 0.17 | 0.08 |
| 10 | 3 | 0.15 | 0.06 |

Experiment 10F

Effect of temperature for Clarification of Xanthomonas Cultures.

Heat treated substrate Xanthomonas cells and Lysobacter B23 lytic compounds were prepared as described in Experiment 10D. One volume of B23 lytic compounds were added to 40 volumes of the substrate (4–5 ml per assay) and then the mixture was incubated at various temperatures for 15, 60 or 180 minutes. The initial A600 of the substrate was 0.84. The decreases in A600 are set forth in Table 18.

Using the change in A600 for the earliest time (15 minutes) as a measure of the initial reaction rate, the most rapid clarification is observed between about 55° C. and 60° C. Longer times at elevated temperatures cause inactivation of the lytic activity, as seen in Experiment 10E. Using the extent of reaction in 180 rain, the overall optimum for temperature is between about 45° C. and 50° C. However, there is a lower amount of activity across the entire temperature range tested. Therefore, for clarification of Xanthomonas cultures the temperature is preferably from about 30° C. to 70° C., and, more preferably, from about 40° C. to 55° C., and, most preferably, at about 45° C.

TABLE 18

| Temperature (°C.) | A600 Duration of assay (min) | | |
|---|---|---|---|
| | 15 | 60 | 180 |
| 30 | 0.64 | 0.41 | 0.11 |
| 40 | 0.50 | 0.13 | 0.06 |
| 45 | 0.43 | 0.08 | 0.04 |
| 50 | 0.36 | 0.07 | 0.04 |
| 50 | 0.34 | 0.07 | 0.05 |
| 55 | 0.27 | 0.13 | 0.12 |
| 55 | 0.31 | 0.10 | 0.07 |
| 58 | 0.28 | 0.13 | 0.12 |
| 60 | 0.28 | 0.17 | 0.15 |
| 62 | 0.32 | 0.21 | 0.18 |
| 65 | 0.38 | 0.29 | 0.23 |
| 70 | 0.52 | 0.38 | 0.34 |

Experiment 10G

Effect of pH for Clarification of Xanthomonas Culture

Heat-treated substrate Xanthomonas cells and Lysobacter B23 lytic compounds were prepared as described in Experiment 10D. One volume of B23 lytic compounds were added to 40 volumes of the substrate (4–5 ml per assay) and then the mixture was incubated at 45° C. for 15, 60 or 180 minutes. The pH for each reaction was adjusted by adding HCl or NaOH. The initial A600 of the substrate was 0.87. The decreases in A600 are set forth in Table 19.

Using the change in A600 for the earliest time (15 minutes) as a measure of the initial reaction rate, the most rapid clarification is observed at pH 8.7. Using the extent of reaction in 180 minutes, the overall optimum for pH is between 8.2 and 8.7. However, there was also substantial activity in the pH range of 6.0 to 9.3, and a lower amount of activity even at pH values as high as 10. Therefore, for clarification of Xanthomonas the pH of the culture is best kept below about 10, and more preferably from about 6 to 9.3.

TABLE 19

| pH | A600 Duration of assay (min) | | |
|---|---|---|---|
| | 15 | 60 | 180 |
| 6.0 | 0.60 | 0.28 | 0.07 |
| 6.5 | 0.51 | 0.19 | 0.06 |
| 7.0 | 0.49 | 0.15 | 0.05 |
| 7.6 | 0.43 | 0.09 | 0.05 |
| 8.2 | 0.37 | 0.07 | 0.05 |
| 8.7 | 0.33 | 0.08 | 0.05 |
| 9.3 | 0.51 | 0.20 | 0.10 |
| 10.0 | 0.77 | 0.68 | 0.58 |

Experiment 10H

Comparison of SO-4 Powder to Lytic Compounds from Lysobacter B23 for Clarification of Xanthomonas Cells in the Presence of Xanthan Gum Heat-treated substrate Xanthomonas cells and Lysobacter B23 lytic compounds were prepared as described in Experiment 10D. However, in this case, the *Xanthomonas campestris* was strain X59, which accumulates xanthan gum in the culture broth. Cultures of strain X59 become very viscous when the amount of glucose is equal to or above about 1% (w/v). The medium for culturing the Xanthomonas was YM, with or without glucose at 10 g/l. SP-4 powder was added to 24 ml of substrate culture to give 500 ppm final concentration. One volume of B23 lytic compounds was added to 40 volumes of the substrate (24 ml per assay). The mixtures were incubated at 30° C. for 1 to 24 hours with rotary shaking at 230 rpm. The initial A600 of the substrate was about 2.3. Typically, the concentrations of xanthan in cultures grown with 1% glucose are about 0.4 to 0.6% (w/v). The results, set forth in Table 20, show that the lytic compounds from Lysobacter B23 were more effective at clarifying Xanthomonas cultures in the presence of xanthan than the alkaline protease SP-4 powder at 500 ppm.

TABLE 20

| Enzyme sample | Xanthomonas X59 culture medium | A600 Duration of assay (min) | | | | |
|---|---|---|---|---|---|---|
| | | 1 | 3 | 6 | 10 | 24 |
| B23 | + glucose | 1.01 | 0.39 | 0.24 | 0.22 | 0.18 |
| | no glucose | 0.37 | 0.19 | 0.13 | 0.11 | 0.10 |
| SP-4 Powder | + glucose | 0.73 | 0.47 | 0.40 | 0.38 | 0.39 |
| | no glucose | 0.21 | 0.18 | 0.17 | 0.16 | 0.16 |

What is claimed is:

1. An extracellular enzyme containing composition obtained by subjecting a strain of bacteria selected from the group consisting of Aeromonas media-like DNA group 5A and Lysobacter species to culturing in a nutrient medium and separating the nutrient broth containing the composition from the bacterial cellular debris, the composition being capable of lysing cells and enzymatically digesting cellular debris in a polysaccharide-producing bacteria in the presence of polysaccharides produced by the polysaccharide-producing bacteria without degrading the polysaccharides.

2. The enzyme composition of claim 1 wherein the strain is Lysobacter enzymogenes subspecies enzymogenes ATCC 55319.

3. The enzyme composition of claim 1 wherein the strain is Lysobacter enzymogenes subspecies enzymogenes ATCC 27796 or Lysobacter enzymogenes subspecies cookii ATCC 29488.

4. The enzyme composition of claim 1 wherein the strain is aeromonas species ATCC 55301.

5. The enzyme composition of claim 1 wherein the polysaccharide-producing bacteria are selected from the group consisting of Xanthomonas campestris, Pseudomonas, Alcaligenes and Beijerinckia indicia.

6. A method for clarifying a mixture of a polysaccharide produced by submerged culturing of bacteria and cellular debris of said bacteria comprising contacting said mixture with the enzyme composition of one of claims 1, 2 or 3 for a time period and under such conditions sufficient to allow enzymatic digestion of said cellular debris.

7. The method of claim 6 wherein the polysaccharide is xanthan and the bacteria is Xanthomonas campestris.

8. The method of claim 6 wherein the contacting is carried out at a temperature in the range from about 20° C. to 80° C.

9. The method of claim 6 wherein the polysaccharide is welan and the cellular debris is from Alcaligenes.

10. The method of claim 6 wherein the strain is selected from the group consisting of Aeromonas media-like DNA group 5A and Lysobacter enzymogenes.

11. The method of claim 6 wherein the strain is selected from the group consisting of Lysobacter enzymogenes ATCC 55319 and Aeromonas species.

12. The method of claim 6 wherein the polysaccharide is recovered from the mixture after the enzymatic digestion.

* * * * *